(12) United States Patent
Volpe et al.

(10) Patent No.: US 7,842,826 B2
(45) Date of Patent: Nov. 30, 2010

(54) PROCESS FOR SYNTHESIZING HALOGENATED DERIVATIVES OF FLUORESCEIN FOR USE IN THE PRODUCTION OF NON-VOLATILE MEMORY DEVICES

(75) Inventors: Maria Viviana Volpe, Pozzuoli (IT); Angela Cimmino, Casagiove (IT); Alessandro Pezzella, Napoli (IT); Aniello Palma, Napoli (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 345 days.

(21) Appl. No.: 11/852,026

(22) Filed: Sep. 7, 2007

(65) Prior Publication Data
US 2008/0061289 A1 Mar. 13, 2008

(30) Foreign Application Priority Data
Sep. 8, 2006 (IT) .......................... MI2006A1713

(51) Int. Cl.
*C07D 311/94* (2006.01)
(52) U.S. Cl. ..................................................... 549/385
(58) Field of Classification Search .................. 549/385
See application file for complete search history.

(56) References Cited

U.S. PATENT DOCUMENTS 4,547,597 A * 10/1985 Louks et al. ................. 568/779

OTHER PUBLICATIONS

Metzger et al. Chemoshpere 43 (2001), 83-87.*
Balalaie et al. Fifth International Electronic Conference on Synthetic Organic Chemistry (ECSOC-5), http://www.mdpi.org/ecsoc-5.htm, Sep. 1-30, 2001.*
Andrews et al., "The Chlorination of Aromatic Hydrocarbons in Carbon Tetrachloride and in Trifluoroacetic Acid," Journal of the American Chemical Society 79: 5169-5174, Oct. 5, 1957.
Andrews et al., "The Influence of Solvent on the Rate of Aromatic Chlorination," Journal of the American Chemical Society 81(5): 1063-1067, Mar. 5, 1959.
Bandyopadhyay et al., "Large conductance switching and memory effects in organic molecules for data-storage applications," Applied Physics Letters 82(8): 1215-1217, Feb. 24, 2003.
Bandhopadhyay et al., "Large Conductance Switching and Binary Operation in Organic Devices: Role of Functional Groups," Journal of Physics and Chemistry B 107(11): 2531-2536, 2003.

Bandyopadhyay et al., "Memory-Switching Phenomenon in Acceptor-Rich Organic Molecules: Impedance Spectroscopic Studies," Journal of Physics and Chemistry B 109(13): 6084-6088, 2005.
Barhate et al., "Simple and Practical Halogenation of Arenes, Alkenes and Alkynes with Hydrohalic Acid/H2O2 (or TBHP)," Tetrahedron 55: 11127-11142, 1999.
Barnett et al., "Trifluoroacetyl Hypohalites as Aromatic Halogenating Agents," Journal of American Chemical Society 94(17): 6129-6134, Aug. 23, 1972.
Jiao et al., "Syntheses of Regioisomerically Pure 5- or 6-Halogenated Fluoresceins," Journal of Organic Chemistry 68 (21): 8264-8267, Oct. 7, 2003.
Karade et al., "Grindstone chemistry: (diacetoxyiodo)benzene-mediated oxidative nuclear halogenation of arenes using NaCl, NaBr or I2," Journal of Chemical Research, pp. 366-368, Jun. 2006.
Keefer et al., "The Trifluoroacetic Acid Catalyzed Chlorination of Aromatic Hydrocarbons in Carbon Tetrachloride. Inhibition by Acetic Acid," Organic and Biological Chemistry 82: 4547-4553, Sept. 5, 1960.
Khan et al., "Monobromination of Deactivated Active Rings Using Bromine, Mercuric Oxide, and Strong Acid," Journal of Organic Chemistry 53: 1799-1800, 1988.
Majee et al., "Electrical bistability in molecular films: transition from memory to threshold switching." Chemical Physics Letters 399: 284-288, 2004.
Nolan et al., "The Zinspy Family of Fluorescent Zinc Sensors: Syntheses and Spectroscopic Investigations," Inorganic Chemistry 43(26): 8310-8317, 2004.
Stock et al., "Rates and Isomer Distributions in the Non-catalytic Chlorination of the Halobenzenes and Certain Halotoluenes in Aqueous Acetic Acid. Partial Rate Factors for the Halogenation of the Halobenzenes," Journal of the American Chemical Society 84(9): 1662-1667, May 5, 1962.
Stock et al., "Rated, Relative Rates and Product Distributions for the Non-catalytic Chlorination of Benzene, Toluene and t-Butylbenzene in Certain Non-aqueous Non-hydroxylic Solvents. The Influence of Solvent on the Reaction and the Baker-Nathan Effect," Journal of the American Chemical Society 83(22): 4605-4609, Nov. 20, 1961.

\* cited by examiner

*Primary Examiner*—D. Margaret Seaman
*Assistant Examiner*—Nizal S Chandrakumar
(74) *Attorney, Agent, or Firm*—Lisa K. Jorgenson; Hai Han; Seed IP Law Group PLLC

(57) ABSTRACT

A process performs solid phase synthesis of halogenated derivatives of fluorescein, and includes reacting fluorescein with a halide MX, wherein M is an alkali metal and X is a halogen, and Oxone® (2 $KHSO_5 \cdot KHSO_4 \cdot K_2SO_4$), at a temperature higher than or equal to 150° C. A structure uses a halogenated derivative of fluorescein selected from the group consisting of 2',4',5'-trichlorofluorescein, 2',4',5',7'-tetrachlorofluorescein, 4',5'-diiodofluorescein diacetate and 2',4',5'-triiodofluorescein as electro-bistable material in a non-volatile memory device.

19 Claims, 5 Drawing Sheets

PROCESS FOR SYNTHESIZING HALOGENATED DERIVATIVES OF FLUORESCEIN FOR USE IN THE PRODUCTION OF NON-VOLATILE MEMORY DEVICES

BACKGROUND

1. Technical Field

The present invention refers in general to the technical field of organic synthesis of compounds with characteristics of electro-bistability, for use in the electronics industry to produce non-volatile memory devices.

In particular, the invention concerns a process for solid phase synthesis of halogenated derivatives of fluorescein, and their use as electro-bistable materials in non-volatile memory devices.

2. Description of the Related Art

Fluorescein and its derivatives are organic, aromatic, heterocyclic molecules derived from xanthene and are characterized by a general molecular structure according to the following formulae (I) and (II):

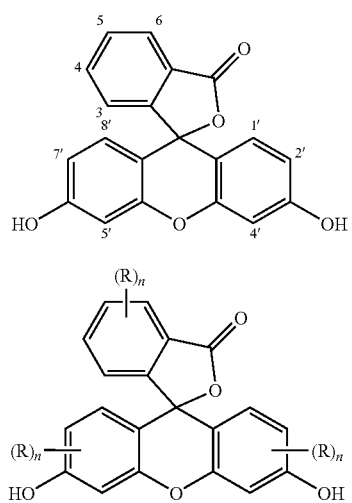

in which formula (I) corresponds to a lactone form of fluorescein and formula (II) corresponds to that of its derivatives, which have one or more various residues or functional groups R in different positions of the aromatic rings (i.e., each n is independently 0, 1, 2, 3 or 4).

The class of fluoresceins comprises highly fluorescent molecules that are used in numerous fields of application, from medicine to microelectronics. From the point of view of safety and environmental compatibility, these materials are not dangerous; indeed, they are biodegradable and non-toxic to man, and, if swallowed or injected into the human body, they are eliminated through the kidneys within 24 hours. See, e.g., http://www.sigmaaldrich.com/catalog/serch/Product-Detail/SIAL/F6377

In medicine, for example, fluorescein and frequently fluorescein-isothiocyanate or FITC, are widely used in immunofluorescence techniques. FITC, for example, is used to label different biomolecules, like for example, immunoglobulins, lectin, different proteins, peptides, nucleic acids, polynucleotides, oligo and polysaccharides. The products thus labeled are used as reactants for dyeing biomolecular sections by affinity, for immunodyeing and for dyeing by in situ hybridization, but also for the dyeing of living cells and for dyeing in flow cytometric methods, as they are not toxic for the host organism. Fluorescein is used, for example, in opthalmology as contrast dye for fluoroangiographic examinations, which study the anatomical alterations of the retina through the intravenous introduction of the dye followed by a photographic sequence of the eye fundus (retina). Moreover, thanks to its characteristically intense fluorescence, even in extremely diluted conditions, the molecule is normally used in the field of hydrogeology as hydrological tracer in the analysis of water tracing in underground basins. See, e.g., Bandiera, F. *Sardegna Speleologica,* 16, (1999).

In the field of microelectronics, on the other hand, it is known from literature that fluorescein and some of its derivatives are promising materials for organic-based non-volatile memory devices.

The increasing miniaturization of the electronic devices has recently also hit the field of non-volatile memories. However, if on the one hand this trend corresponds to a substantial increase in the integration density on a chip, in parallel it requires substantial economic engagement aimed at overcoming a series of technological limitations. The use of organic materials as memory elements and the adoption of process technologies, alternative to those currently in use for semiconductor (e.g., silicon) devices, are greatly motivated by the possibility of overcoming the aforementioned technological limitations and pushing the comminution up to molecular level.

It is known from literature that some organic molecules can have logic functions and memory functions, due to switch phenomena between stable states. In particular, the physical property of an organic material that is most suitable for use as memory element is electro-bistability. From the physical point of view, an electro-bistable material is defined as a material that shows a variation in electrical conductivity passing from a highly resistive state to a conductive state under the effect of an electrical field, as shown in FIG. 1.

In terms of architecture, the innovative memory devices, having organic materials as memory elements, are made according to a "pad size" structure, resulting from the repetition of "cross-point" memory cells. The organic memory element, in the form of a thin film, is placed between two electrodes, made of metal and/or conductive oxides, according to the schemes of FIG. 2 and of FIG. 3.

This type of device can be made by using fairly well established low-cost process technologies, both in terms of the deposition of the electrodes and of the memory element. In particular, the pattern of bottom electrodes can be made by using physical vapor deposition (PVD, sputtering) technologies and the deposition of the memory element, in the form of a thin film can be carried out through low-temperature vapor phase (PVD) processes or more frequently through spin-coating and therefore through a liquid phase deposition technology. Indeed, it is known that organic materials can be effectively manipulated from liquid phase thanks to their high solubility in low-boiling point organic solvents (chlorinated hydrocarbons, alcohol hydrocarbons, ethers, esters, etc). The deposition, which is the last step of the assembly process of the device, can analogously be carried out through physical vapor deposition (PVD, sputtering) technologies.

For an electro-bistable organic material to be used as memory element, the transition between the resistive and conductive states should suitably take place in standard conditions of temperature and pressure, the potential range should be fairly narrow (about 10 V), the ratio between the resistivities of the two states (ON/OFF) should suitably be at least by a factor of $10^3$, the transition should take place in short times (<100 ns) and finally the number of writing/reading/cancellation cycles should be at least $10^4$. In literature, different materials are disclosed that display such a property. The physical mechanisms responsible for electro-bistability can include structural rearrangements, through changes in configuration, modifications of the conjugation of the mobile π-electrons, via electroreduction, or both factors.

Fluorescein, and in particular, some haloderivatives of Fluorescein, as shown in the following formulae, display properties of electro-bistability with electrical performance, relative to non-volatile memory devices, that improves according to the number of electron-withdrawing substituents (e.g., halogens) on the skeleton of the molecule. See, e.g., Bandyopadhyay, A. et al, Applied Physics Letters, 82,1215, (2003); Bandhopadhyay, A. et al, J. Phys. Chem. B, 107, 2531, (2003); Majee, S. K. et al, Chem. Phys. Lett, 399, 284, (2004); Bandyopadhyay, A. et al, J. Phys. Chem. B, 109, 6084, (2005).

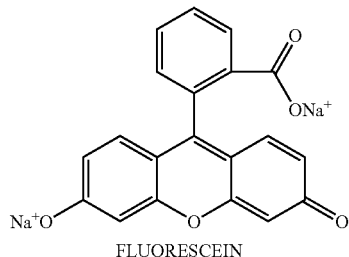

(Fl)

FLUORESCEIN

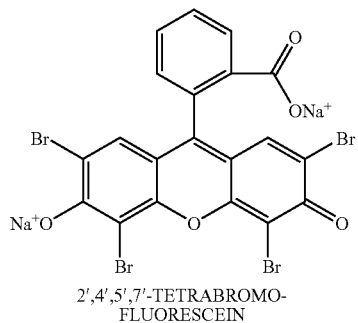

(Eosin Y)

2',4',5',7'-TETRABROMO-FLUORESCEIN

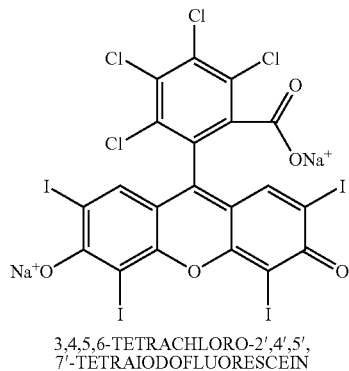

(Rose Bengal)

3,4,5,6-TETRACHLORO-2',4',5',7'-TETRAIODOFLUORESCEIN

Prototypes of memory cells based on fluorescein and its derivatives have exhibited interesting electrical characteristics: by applying an increasing potential difference in the range 0-4 V, an extremely low current is recorded due to the high resistivity of the molecules (OFF state). In particular, for a device having a thin film of Rose Bengal as the memory element, when the potential is above about 4 V, a clear increase in current is recorded due to a decrease in resistivity (ON state) that lasts until a negative voltage corresponding to −4V is applied, indicating that the material goes back to OFF state due to high resistivity, and the datum is "cancelled" (FIG. 4).

Analogous results have been obtained on devices having thin films of fluorescein and of Eosin Y as memory elements. The performance of the three devices, having fluorescein, Eosin Y and Rose Bengal, respectively, as memory elements, is shown in Table 1. See, supra. The table highlights an increasing trend of the ON/OFF ratio of fluorescein to Rose Bengal and this phenomenon is in relation to the number of electron-withdrawing substituent groups on the skeleton of the molecule. The presence of the electron-withdrawing groups in the two halogen-derivatives of fluorescein (Eosin Y and Rose Bengal) draws electrons, which has the consequence of perturbing the aromatic conjugation and therefore decreasing the conductivity of the OFF state. Such an effect leads to an increase in the ON/OFF ratio, proportionally to the number and nature of the electron-withdrawing groups present.

TABLE 1

| Molecule | Structure | ON/OFF | Cycles |
| --- | --- | --- | --- |
| Fluorescein | 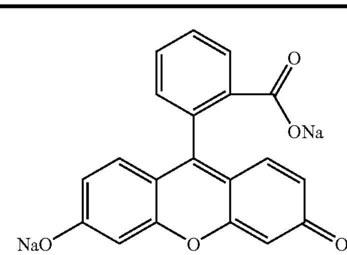 | 4 | >10⁶ |

TABLE 1-continued

| Molecule | Structure | ON/OFF | Cycles |
| --- | --- | --- | --- |
| Eosin Y 2',4',5',7'-tetrabromofluorscein | 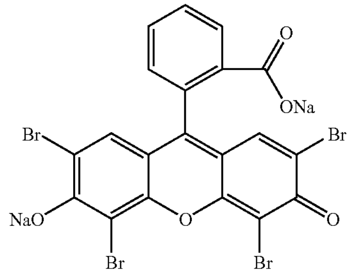 | 9800 | >10⁶ |
| Rose Bengal 3,4,5,6-tetrachloro-2',4',5',7'-tetraiodo-fluorescein | 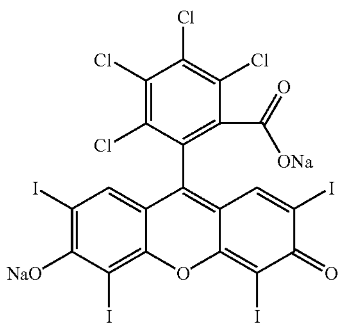 | 105 | >10⁶ |

Although in the current state of the art there is no interpretative model of the phenomenon of bistability on a molecular basis, it is possible, in light of the data from literature, to identify in some functional groups and in certain structural features some important elements for achieving bistability. In particular, aromatic rings carrying electron-rich and/or electron-withdrawing substituents and the presence of hindered diphenyl systems constitute a recurrent theme in molecules exhibiting bistability. Moreover, the organization of bistable molecules into regular domains within films influences the electrochemical parameters of the devices made, in particular, films having highly regular domains display better ON/OFF range values and relative resistance ratio values between the resistive state and conductive state.

The halogenations of aromatic organic molecules are electrophilic substitution reactions, which are conducted, conventionally, in liquid phase and based upon the use of hydrohalogenic acids or of molecular halogens as halogenating agents. See, e.g., http://v3.espacenet.com/results?AB=halogenation+of+phenols&sf=q&FIRST=1&CY=gb&LG=en&DB=EPODOC&st=AB&kw= halogenation+of + phenols&=&=&=&=&=*Tetrahedron* 55 (36), pp. 11127-11142 (1999); *J. Am. Chem. Soc.* 84,1661 (1962); *J. Am. Chem. Soc.* 81,1063 (1959); *J. Am. Chem. Soc.* 82, 4547 (1960); and *J. Am. Chem. Soc.* 79, 5169 (1957). The halogenation rates and the reactivity of halogens towards organic substrates depend upon numerous factors: mainly the halogen and the number, type and position of the substituent groups in the organic substrate. Generally, molecular chlorine and bromine are highly reactive towards aryl substrates. "Aryl substrate" refers to an aromatic molecule having delocalized π-electrons. Typically, Lewis acids are used to increase the rate of the reactions. Molecular fluorine reacts very violently and the reaction conditions always have to be carefully controlled, and finally molecular iodine only reacts with very reactive aromatic substrates.

The role of Lewis acids of the HA type is to promote the aromatic electrophilic substitution process by assisting in breaking the X—X link of the halogen molecule ($X_2$), as shown in the following chlorination scheme:

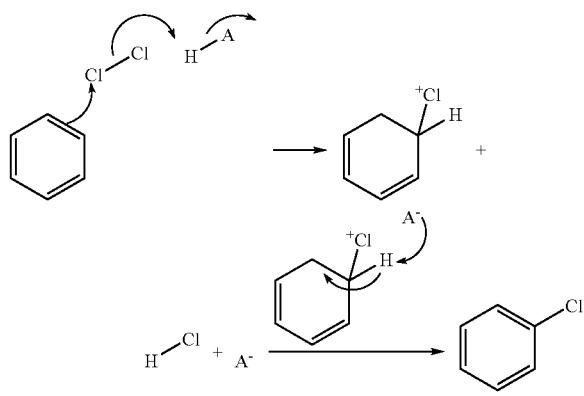

The catalytic mechanism of Lewis acids of general formula $MX_n$, is analogous to that of HA acids. For chlorination reactions, metal salts such as $ZnCl_2$ and $FeCl_3$ or elementary metals, are generally used as Lewis acids, and molecular chlorine is generally used as the chlorinating agent, as shown in the following scheme:

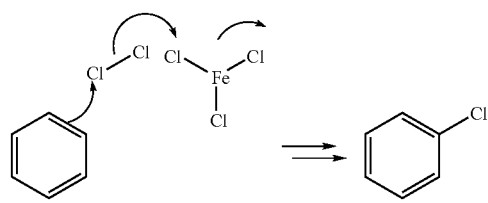

Other factors that impact the halogenation process in liquid phase include the proticity and polarity of the solvent. For example, chlorinations are much faster in polar solvents than in non-polar solvents. See, e.g., *J. Am. Chem. Soc.* 83, 4605 (1961).

Similarly to what has been described for the chlorination process, numerous aromatic substrates can be brominated. For example, phenyl derivatives and aniline derivatives in particular are reactive to bromination. The use of Lewis acids, as catalysts, also promotes the bromination of deactivated aromatic substrates, i.e., those functionalized with electron-withdrawing substituents, like nitro-groups and cyano-groups. See, e.g., *J. Org. Chem.* 53, 1799 (1988).

Another known synthetic scheme discloses the use of mercury acetate or mercury trifluoroacetate as catalysts. The synthetic strategy on which it is based involves the formation of acetyl or trifluoroacetyl hypohalogenites as the halogenating species and generally it is adopted for the halogenation of very deactivated aryl substrates. See, e.g., *J. Am. Chem. Soc.* 94, 6129 (1972). The formation of acetyl or trifluoroacetyl hypohalogenites is regulated by the equilibrium displayed in the following scheme:

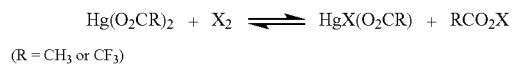

(R = CH$_3$ or CF$_3$)

As far as the iodination reactions are concerned, in addition to the use of molecular iodine in the presence of Lewis acids, there are alternative synthetic schemes using mixtures of metal iodide and cerium ammonium nitrate [Ce(NH$_3$)$_2$(NO$_3$)$_6$] as iodinating agents, or mixtures of molecular iodine and silver and mercury salts.

Recently, a halogenation procedure of aromatic substrates, in particular arenes, in solid phase has been developed that uses metal halides as halogenating agents and diacetoxyiodobenzene as oxidizing agent. However, at this point in time there is no example of halogenation in solid phase of xanthene derivatives. See, e.g., *J. Chem. Res.*, 6, 366 (2006). The halogenation processes that have been used up to now to synthesize halogen derivatives of fluorescein are invariably carried out in a liquid phase with the help of a solvent, which imposes numerous process stages, such as extraction, dehydration, filtering processes, etc., which in addition to being time-consuming and costly, can cause product losses. Moreover, such syntheses in liquid phase often require protection of functional groups and subsequent deprotection of them, which can substantially lower the reaction yields. See, e.g., *J. Org. Chem.*, 68, 8264 (2003), and *In. Chem.*, 43(26), 8310 (2004).

BRIEF SUMMARY

One embodiment provides a process for obtaining halogenated derivatives of fluorescein that overcame the drawbacks linked to the processes of the prior art.

More specifically, the process for synthesizing halogenated derivatives of fluorescein comprises reacting fluorescein with a halide (MX), wherein M is an alkali metal and X is a halogen, and an oxidizing agent, such as Oxone® (2 KHSO$_5$.KHSO$_4$.K$_2$SO$_4$) in solid phase, at a temperature higher than or equal to 150° C.

In a further embodiment, the reaction is conducted at a temperature of between 170° C. and 250° C., advantageously at 180° C.-220° C.

In various embodiments, the same number of equivalents of MX and of Oxone® are used and the ratio between the equivalents of fluorescein and either MX or Oxone® is between 1:20 and 1:10, advantageously, 1:16.

The reaction is generally conducted for 8-16 hours, advantageously 10-12 hours.

Preferably, the reaction is run by heating a finely powdered homogeneous mixture of fluorescein, MX and Oxone® to the temperature indicated above.

In another embodiment, chloroderivatives of fluorescein can be obtained by a process comprising reacting fluorescein with FeCl$_3$ in solid phase, at a temperature higher than or equal to 130° C.

In various embodiments, the reaction is run at a temperature of between 140° C. and 160° C., advantageously at 150° C.

In certain embodiments, the ratio between the equivalents of fluorescein and of FeCl$_3$ is between 1:6 and 1:10, advantageously 1:8.

The reaction is generally conducted for 8-16 hours, advantageously 10-12 hours.

Preferably, the reaction is run by heating a finely powdered homogeneous mixture of fluorescein and FeCl$_3$ to the temperature indicated above.

The reactions in solid phase are characterized by high yields, generally over 80%. Moreover, the absence of solvents makes the synthesis easy to carry out, inexpensive and above all easy to industrialize, because it involves only a mixing step and a reaction step at non-critical temperature.

Other embodiments describe the use of some halogenated derivatives of fluorescein as electro-bistable materials in non-volatile memory devices. These fluorescein derivatives can be obtained by the process according to the invention, and include, e.g., 2',4',5'-trichlorofluorescein (3Cl—F), 2',4',5',7'-tetrachlorofluorescein (4Cl—F), 4',5'-diiodofluorescein diacetate (2I—F—Ac), 2',4',5'-triiodofluorescein (3I—F) and 2',4',5',7'-tetrabromofluorescein (4Br—F).

Of the compounds listed above only the disodium salt of 2',4',5',7'-tetrabromofluorescein is available on the market (Eosin Y).

A further embodiment describes a non-volatile memory device, comprising at least one top conductive electrode and a bottom conductive electrode that enclose an electro-bistable organic memory element, in which the electro-bistable organic memory element comprises a halogenated derivative of fluorescein selected from the group consisting of 2',4',5'-trichlorofluorescein, 2',4',5',7'-tetrachlorofluorescein, 4',5'-diiodofluorescein diacetate and 2',4',5'-triiodofluorescein.

Advantageously, the memory device is made with "cross-point" structure of the type illustrated in FIGS. 2 and 3, the electro-bistable organic memory element being in the form of a thin film.

The following Table 2 shows the identifying data of the aforementioned compounds.

TABLE 2

| Molecule | CA Index Name | CA Registry Number | Commercial Availability |
|---|---|---|---|
| 2',4',5'-trichlorofluorescein (3Cl—F) | 2',4',5'-trichloro-3',6'-dihydroxy-Spiro[isobenzofuran-1(3H),9'-[9H]xanthen]-3-one | 2861-41-8 | NO |

TABLE 2-continued

| Molecule | CA Index Name | CA Registry Number | Commercial Availability |
|---|---|---|---|
| 2',4',5',7'-tetrachlorofluorescein (4Cl—F) | 2',4',5',7'-tetrachloro-3',6'-dihydroxy-Spiro[isobenzofuran-1(3H),9'-[9H]xanthen]-3-one, | 2320-38-9 | NO |
| 4',5'-diiodofluorescein diacetate (2I—F—Ac) | Fluorescein,4',5'-diiodo, diacetate | 3535-90-8 | NO |
| 2',4',5'-triiodofluorescein (3I—F) | 3',6'-dihydroxy-2',4',5'-triiodo-Spiro[isobenzofuran-1(3H),9'-[9H]xanthen]-3-one, | 56254-06-9 | NO |
| 2',4',5',7'-tetrabromofluorescein (4Br—F) | 2',4',5',7'-tetrabromo-3',6'-dihydroxy-Spiro[isobenzofuran-1(3H),9'-[9H]xanthen]-3-one, disodium salt | 17372-87-1 | SI Eosin Y |

CA: Chemical Abstract

DETAILED DESCRIPTION

For the synthesis of halogen derivatives of fluorescein with MX and Oxone®, the following is generally carried out.

A mixture of lactonic Fluorescein (1 equivalent) and of a halide of an alkali metal MX (16 equivalents), and Oxone® (2 $KHSO_5.KHSO_4.K_2SO_4$) (10-20 equivalents) is finely ground in a mortar. The homogeneous mixture thus obtained is placed in an oven at 170-250° C. for 8-16 hours.

For all halogenations (chlorination, bromination and iodination) the fluorescein is totally consumed and the respective halogenated products are formed, with practically quantitative yields (~100%). Where necessary, the products were purified by chromatography on silica gel. All of the products were characterized through structural investigation techniques (ElectroSpray Ionization Mass Spectrometry ESI MS, $^1$H-NMR and $^{13}$C-NMR).

The present invention shall be described further with reference to some examples provided hereafter by way of illustration and not of limitation.

EXAMPLE 1

Chlorination Reaction of Fluorescein

A mixture of the lactonic form of fluorescein (1 equivalent), 16 equivalents of NaCl, and 16 equivalents of Oxone® (2 $KHSO_5.KHSO_4.K_2SO_4$) is crushed in an agate mortar until a homogeneous and finely ground mixture is obtained. The solid mixture is placed in an oven at 200° C. for 12 hours to obtain with an overall yield of 80% (58% 4Cl—F, 22% 3Cl—F) the chlorine derivatives shown in the following scheme.

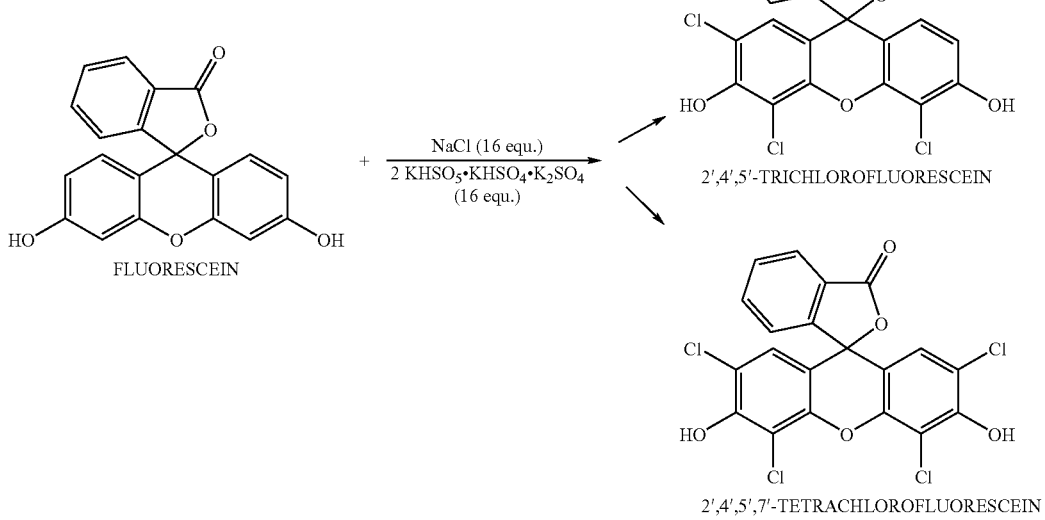

The two chloroderivatives are separated through chromatographic techniques and characterized through Mass Spectrometry ESI and spectroscopic techniques ($^1$H-NMR and $^{13}$C-NMR). In particular, 3Cl—F: ESI MS (−): 433.1 M$^-$H$^-$; $^1$H NMR (CH$_3$OD) 6.86 ppm (s, 1' H); 6.71 ppm (d, J=8.0 Hz, 7' H); 6.75 ppm (d, J=8.0 Hz, 8' H); 7.33 (d, J=8.0; Hz, 3H); 7.74 (ddd, J=8.0; 8.0; 1.2 Hz, 5H) 7.78 (ddd, J=8.0; 8.0; 1.2 Hz, 4H), 8.13 ppm (dd, J=8.0; 1.2 Hz 6H). 4Cl—F: ESI MS (−): 466.8 M$^-$H$^-$; $^1$H NMR(CH$_3$OD) 7.04 ppm (s, 1' H and 8' H); 7.326 (dd, J=8.0;3.6 Hz 3H); 7.63 (m 4H and 5H) 8.23 (dd, J=8.0; 3.6 Hz 6H).

Figure 6:
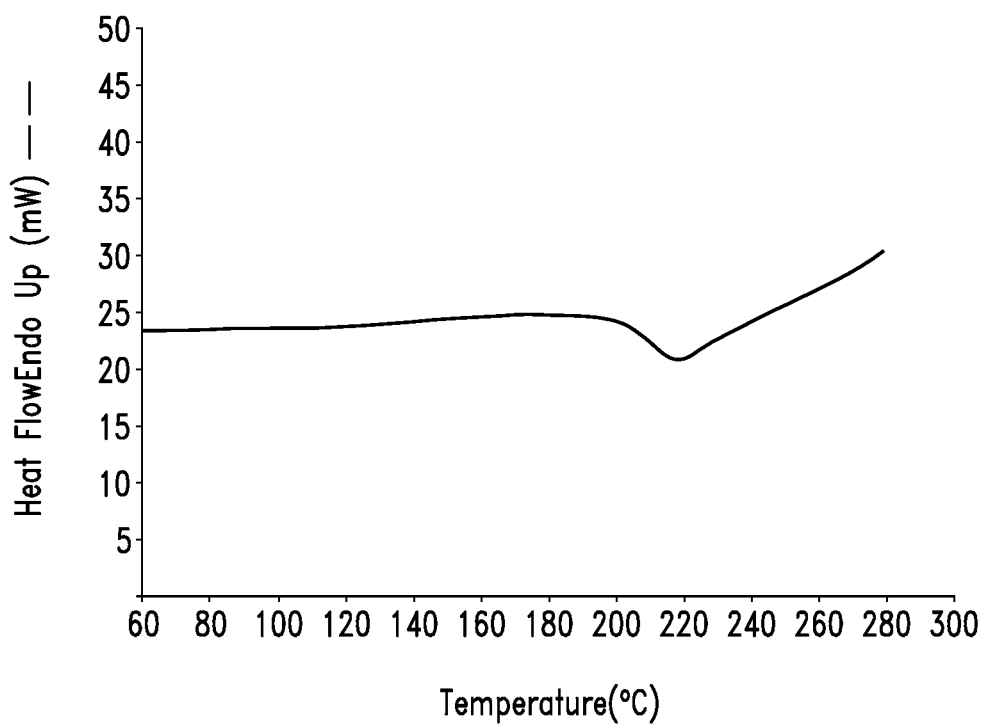
FIG. 6 is a DSC thermogram of 2',4',5'-trichlorofluorescein.
Figure 7:
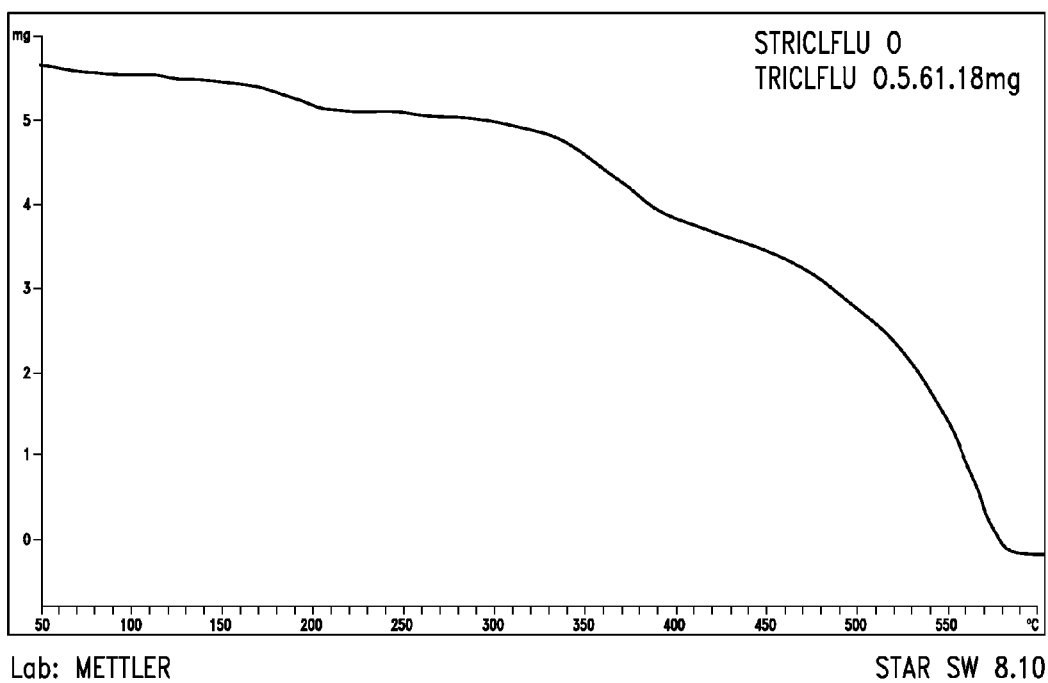
FIG. 7 is the TGA thermogram of 2',4',5'-trichlorofluorescein.

3Cl—F was also characterized through thermal analysis techniques (Differential Scanning Calorimetry—DSC and ThermoGravimetric Analysis—TGA) from which the melting point, $T_f$: 215° C. is obtained. See in particular FIGS. 6 and 7.

EXAMPLE 2

Bromination Reaction of Fluorescein

A mixture of the lactonic form of fluorescein (1 equivalent), 16 equivalents of NaBr, and 6 equivalents of Oxone® (2 KHSO$_5$.KHSO$_4$.K$_2$SO$_4$) is crushed in an agate mortar until a homogeneous and finely ground mixture is obtained. The solid mixture is placed in an oven at 200° C. for 12 hours, to obtain with an overall yield of about 100%, the product shown in the following scheme.

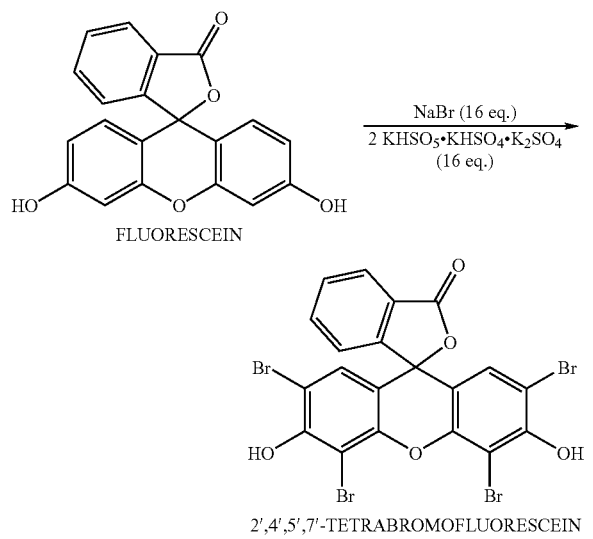

2',4',5',7'-TETRABROMOFLUORESCEIN

With total consumption of the fluorescein, the bromination reaction leads to the formation of a single product, tetrabromofluorescein (4Br—F), the disodium salt of which is commercially known as Eosin Y. The final reaction mixture is diluted in water and the product is extracted from the mixture with ethyl acetate.

The product is characterized by Mass Spectrometry ESI and spectroscopic techniques ($^1$H-NMR and $^{13}$C-NMR). In particular, 4Br—F: ESI MS (+): 670.4 M$^+$H$^+$; $^1$H NMR (CH$_3$OD) 7.04 ppm (s 1' H and 8' H); 7.23 (d, J=8.0 Hz 3 H); 7.72 (ddd, J=8.0; 8.0; 1.2 Hz 5H) 7.79 (ddd, J=8.0; 8.0, 1.2 Hz 4H) 8.09 ppm (d, J=8.0 Hz 6H).

EXAMPLE 3

Iodination Reaction of Fluorescein

A mixture of the lactonic form of fluorescein (1 equivalent), 16 equivalents of NaI, and 16 equivalents of Oxone® (2 KHSO$_5$.KHSO$_4$.K$_2$SO$_4$), is crushed in an agate mortar until a homogeneous and finely ground mixture is obtained. The solid mixture is placed in an oven at 200° C. for 12 hours.

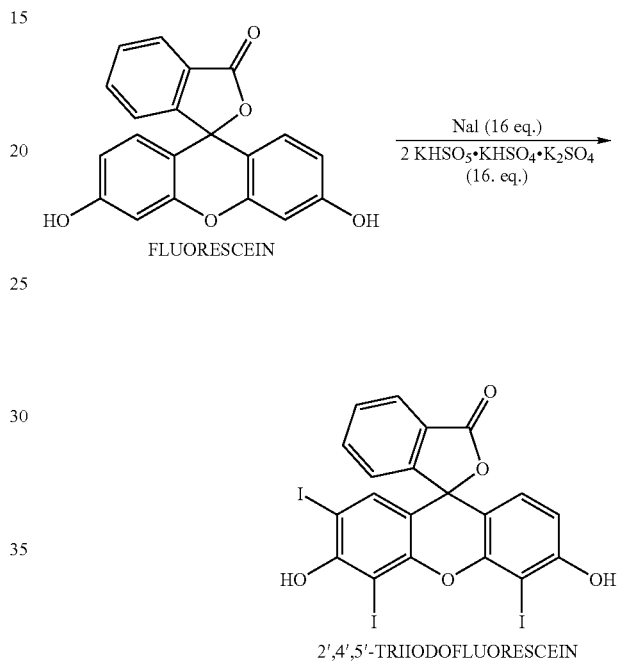

2',4',5'-TRIIODOFLUORESCEIN

The iodination reaction leads to the formation of two products, a main one, 2',4',5'-triiodofluorescein (3I—F, about 70%) and a secondary one, tetraiododerivative (about 30%) which partly decomposes in the work-up of the mixture. Also in this case there is total consumption of the Fluorescein and a substantially quantitative overall yield. The product is characterized by Mass Spectrometry ESI and spectroscopic techniques ($^1$H-NMR and $^{13}$C-NMR). In particular, 3I—F: ESI MS (−): 709.0 M$^-$H$^-$; $^1$H NMR (CH$_3$OD); 6.75 ppm (d, J=8.0 Hz 7' H); 6.79 ppm (d, J=8.0 Hz 8' H); 7.34 (d, J=8.0 Hz 3H); 7.35 (s, 1' H) 7.78 (m, 4H and 5H) 8.15 (dd, J=8.0; 1.2 Hz 6H).

The next step involves acetylation of the above reaction mixture with a combination of acetic anhydride and pyridine as catalyst (acetic anhydride being in excess of pyridine by 20 to 1) and the reaction takes place at room temperature under magnetic agitation for 12 hours. A single product, 4',5'-diiodofluorescein diacetate (2IAcF), is formed, as shown in the following scheme. The solution is treated with methanol and/or ethyl acetate and concentrated under vacuum. The product is characterized by spectroscopic techniques, in particular, 2IAcF: ESI MS (+): 668.6 M$^+$H$^+$; $^1$H NMR (CH$_3$OD) 6.84 ppm (d, J=8.0 Hz 2' H and 7' H), 6.88 ppm (d, J=8.0 Hz 1' H and 8' H), 7.20 ppm (d, J=8.0 Hz 3H) 7.65 ppm (ddd, J=8.0; 8.0; 1.2 Hz, 5H), 7.71 (ddd, J=8.0; 8.0; 1.2 Hz, 4H), 8.03 (d, J=8.0, 6H)

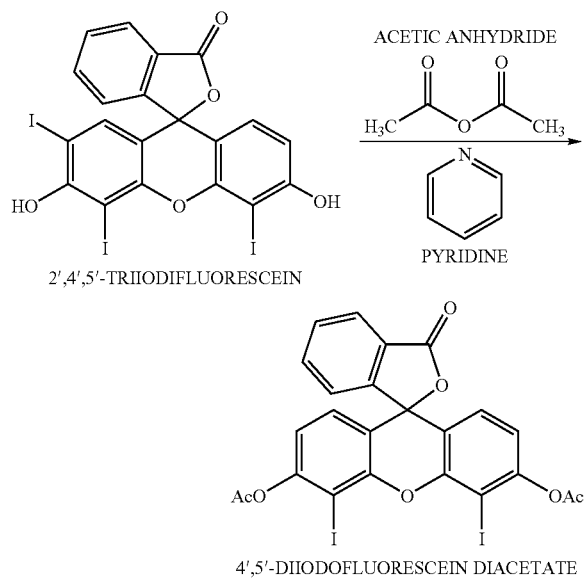

2',4',5'-TRIIODIFLUORESCEIN

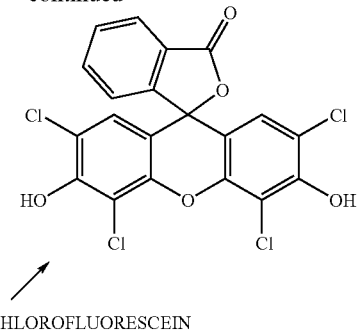

4',5'-DIIODOFLUORESCEIN DIACETATE

EXAMPLE 4

Synthesis of Chlorine Derivatives of Fluorescein with FeCl₃

The lactonic fluorescein (1 equivalent) and FeCl₃ (8 equivalents) are crushed in an agate mortar until a homogeneous and finely ground mixture is obtained. The solid mixture is placed in an oven at 150° C. for 12 hours. The fluorescein is totally consumed and two products, 2',4',5',-trichlorofluorescein and 2',4',5',7'-tetrachlorofluorescein are formed. The scheme of the reaction is shown hereafter.

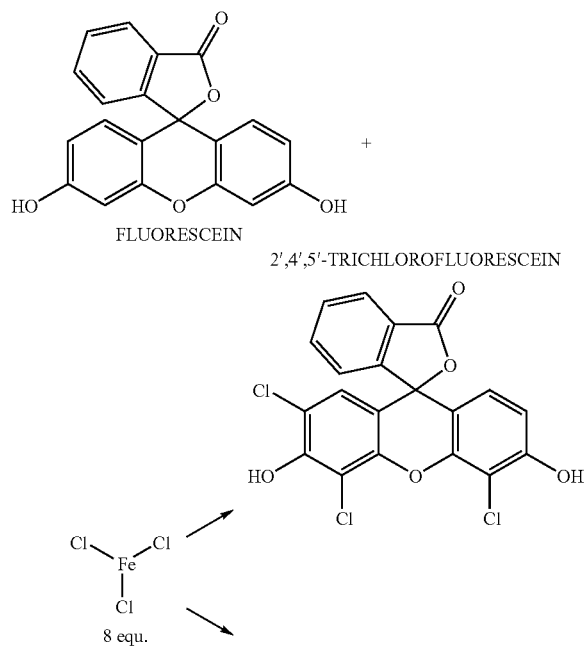

2',4',5'-TETRACHLOROFLUORESCEIN

The products are separated by chromatography on silica gel and characterized with mass Spectrometry, $^1$H-NMR and $^{13}$C-NMR to define the nature and the functionalization positions. The overall yield of the reaction is 90% (4Cl—F 60%, 3Cl—F 30%).

Electrical Characterization of 2',4',5'-Trichlorofluorescein

The halogenated derivatives of fluorescein have displayed interesting properties of bistability in applications of non-volatile memories and as already illustrated with reference to Table 1. An increase in the number of halogen groups corresponds to an increase in the electron-withdrawing force of the halogen(s) on the skeleton of the fluorescein, leading to an increase in the value of the ON/OFF ratio (from 4 for Fluorescein to $10^5$ for Rose Bengal). Therefore, the halogenated molecules described above are expected to display interesting properties of bistability (at least no less than that of the non-functionalized fluorescein).

In order to confirm that the synthesized materials are electro-bistable and therefore can be applied for use in non-volatile memory devices, preliminary electrical characterization tests have been performed on 2',4',5',-trichlorofluorescein (3Cl—F).

3Cl—F was deposited by spin-coating (speed of 2500 rpm for 60" and acceleration 2) on glass substrates coated with ITO (1 cm×1 cm, previously washed in acetone and isopropyl alcohol and dried with a flow of nitrogen). The solution used for deposition has a concentration of 0.2M of 3Cl—F in methanol.

Figure 1:
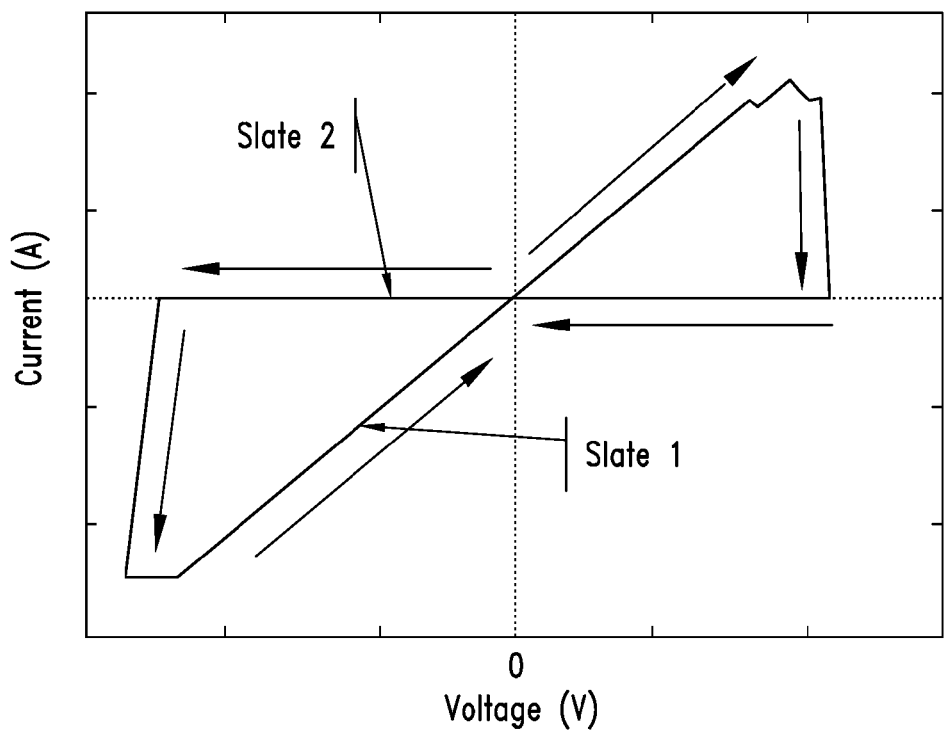
FIG. 1 is a graph illustrating the typical characteristic I/V of an electro-bistable organic material.
Figure 2:
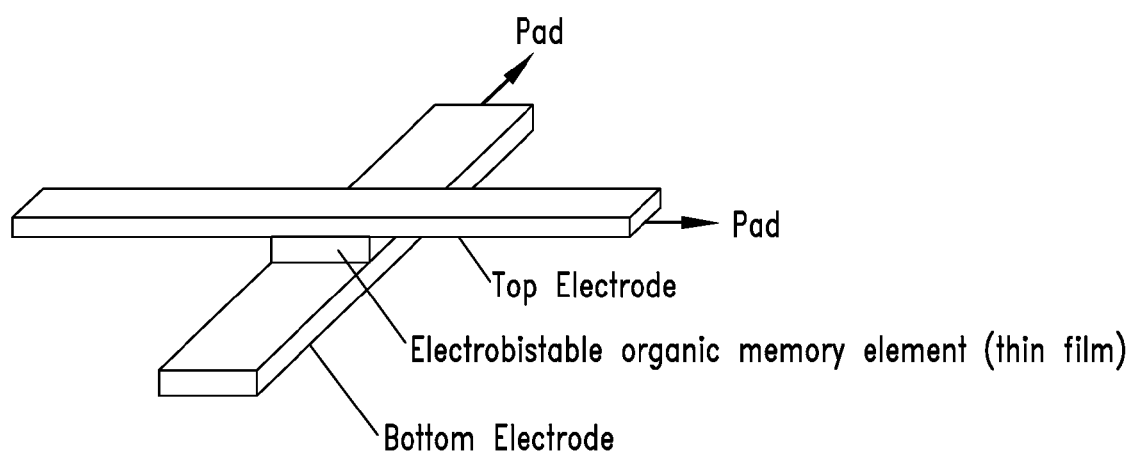
FIG. 2 schematically represents the "cross-point" structure of a non-volatile memory cell having an electro-bistable organic material as memory element.
Figure 3:
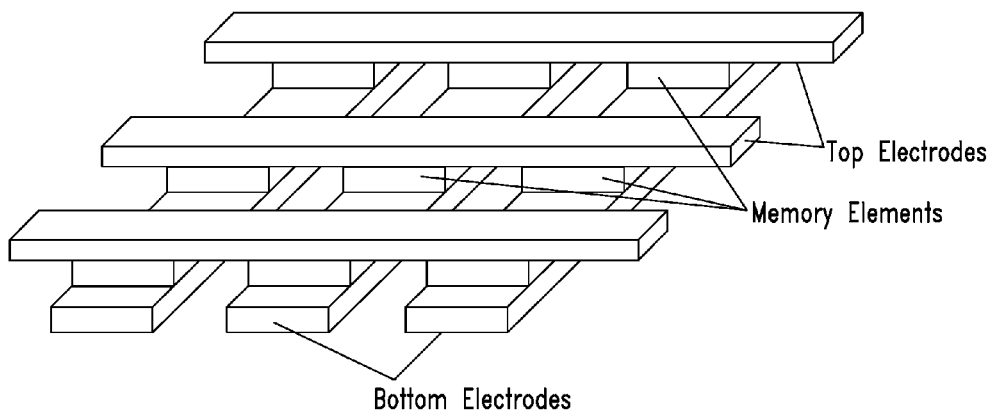
FIG. 3 illustrates a "pad-size" non-volatile memory device.
Figure 4:
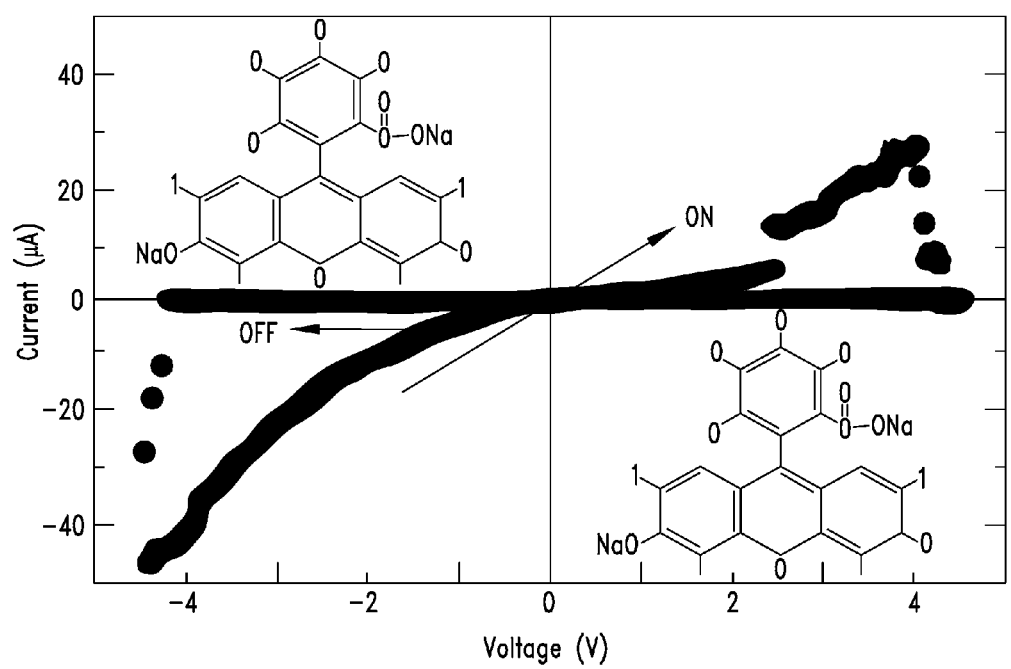
FIG. 4 illustrates the characteristic I/V of devices based upon Rose Bengal film that shows the presence of the two conductive states.
Figure 5:
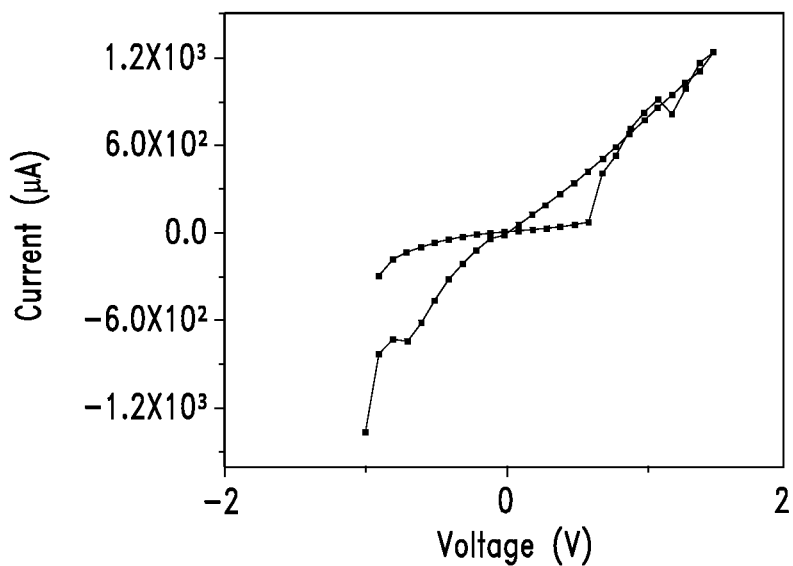
FIG. 5 illustrates the characteristic I/V of the series of two memory cells (Ag/3Cl—F/ITO+ITO/3Cl—F/Ag).
Figure 8:
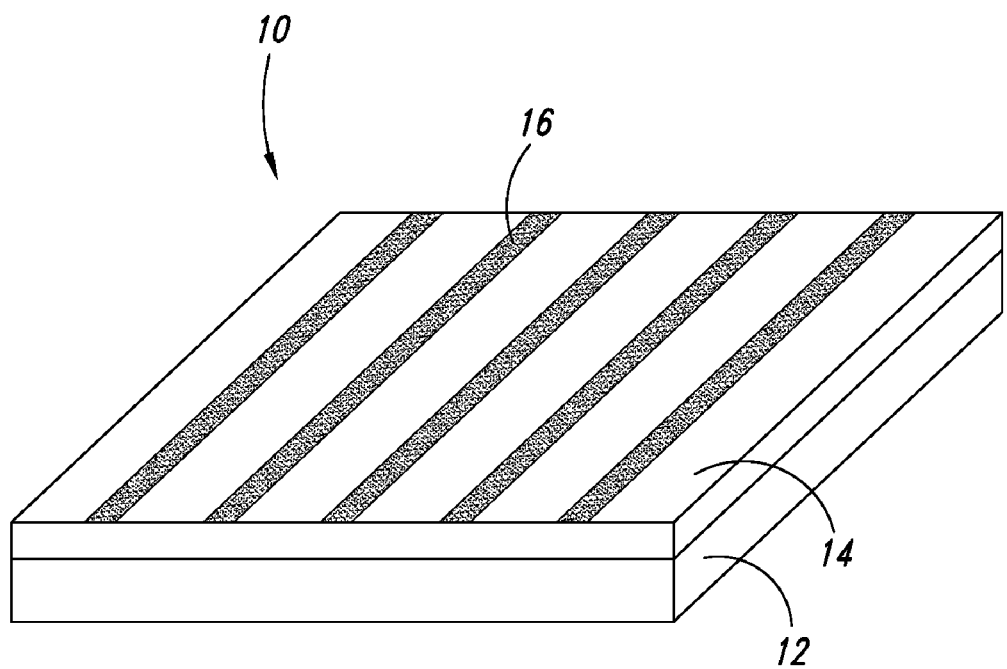
FIG. 8 illustrates an embodiment in which a structure in sandwich and "pad-size" configuration is coated with 3Cl—F as an electro-bistable material.

The characterization was carried out on a device 10 (shown in FIG. 8) in sandwich and "pad-size" configuration. The device 10 comprises an unpatterned bottom electrode of ITO 12 having a 3Cl—F coating 14. A top electrode 16 of Ag is deposited by sputtering in the form of thin lines with spacing of about 100 µm. In order to electrically characterize the material, a cryogenic Probe Station and a picoAmmeter (Keithley 487) were used. By contacting the tips of the Probe Station with two electrodes of Ag the current-voltage characteristic shown in FIG. 5 was obtained. Such a characteristic, which can be traced to the series of two memory cells (Ag/3Cl—F/ITO+ITO/3Cl—F/Ag), shows the electro-bistable behavior of the material suitable for non-volatile memory devices.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process for synthesizing halogenated derivatives of fluorescein, comprising reacting fluorescein with a halide MX, wherein M is an alkali metal and X is a halogen, and 2 $KHSO_5 \cdot KHSO_4 \cdot K_2SO_4$ in solid phase, at a temperature higher than or equal to 150° C.

2. The process according to claim 1, wherein said reacting runs at a temperature of between about 170° C. and 250° C.

3. The process according to claim 2, wherein a same number of equivalents of MX and of 2 $KHSO_5 \cdot KHSO_4 \cdot K_2SO_4$ are used.

4. The process according to claim 3, wherein a ratio between the equivalents of fluorescein and of each one of MX and 2 $KHSO_5 \cdot KHSO_4 \cdot K_2SO_4$ is between about 1:20 and 1:10.

5. The process according to claim 4, wherein said ratio is equal to about 1:16.

6. The process according to claim 2 wherein the reacting is carried out at a temperature of between about 180° C. and 220° C.

7. The process according to claim 1, wherein said reacting is run for about 8-16 hours.

8. The process according to claim 7 wherein the reacting runs for about 10-12 hours.

9. The Process according to claim 1, further comprising forming a finely powdered homogeneous mixture of fluorescein, MX and 2 $KHSO_5 \cdot KHSO_4 \cdot K_2SO_4$.

10. A process for synthesizing chlorine derivatives of fluorescein, comprising reacting fluorescein with $FeCl_3$ in solid phase at a temperature higher than or equal to 130° C.

11. The process according to claim 10, wherein said reacting runs at a temperature of between about 140° C. and 160° C.

12. The process according to claims 10, wherein from about 6 to 10 equivalents of $FeCl_3$ are used for each equivalent of fluorescein.

13. The process according to claim 12, wherein 8 equivalents of $FeCl_3$ are used for each equivalent of fluorescein.

14. The process according to claim 10, wherein the reacting runs for about 8-16 hours.

15. The process according to claim 10, further comprising forming a finely powdered homogeneous mixture of fluorescein and $FeCl_3$.

16. A process for halogenating fluorescein comprising:
   mixing fluorescein, an alkali metal halide, and an oxidizing agent to provide a reaction mixture in the absence of any solvent, wherein the oxidizing agent is 2 $KHSO_5 \cdot KHSO_4 \cdot K_2SO_4$; and
   heating the reaction mixture to form fluorescein substituted with one or more halogens.

17. The process of claim 16 further comprising finely grinding the reaction mixture prior to heating.

18. The process of claim 16 wherein the alkali metal halide is sodium chloride, sodium bromide or sodium iodide.

19. The process of claim 16 wherein the fluorescein substituted with one or more halogens is 2',4',5'-trichlorofluorescein, 2',4',5',7'-tetrachlorofluorescein, 4',5'-diiodofluorescein diacetate, 2',4',5'-triiodofluorescein or 2',4',5',7'-tetrabromofluorescein.

* * * * *

UNITED STATES PATENT AND TRADEMARK OFFICE
CERTIFICATE OF CORRECTION

PATENT NO. : 7,842,826 B2
APPLICATION NO. : 11/852026
DATED : November 30, 2010
INVENTOR(S) : Maria Viviana Volpe et al.

It is certified that error appears in the above-identified patent and that said Letters Patent is hereby corrected as shown below:

Title Page, Item 56

"Jiao et al., "Syntheses of Regioisomerically Pure 5- or 6- Halogenated Flouresceins," Journal of Organic Chemistry 68 (21): 8264-8267, Oct. 7, 2003." should read as, -- Jiao et al., "Syntheses of Regioisomerically Pure 5- or 6- Halogenated Flouresceins," Journal of Organic Chemistry 68 (21): 8264-8267, Oct. 17, 2003.--

"Stock et al., "Rated, Relative Rates and Product Distributions for the Non-catalytic Chlorination of Benzene, Toluene and t-Butylbenzene in Certain Non-aqueous Non-hydroxylic Solvents. The Influence of Solvent on the Reaction and the Baker-Nathan Effect," Journal of the American Chemical Society 83 (22): 4605-4609, Nov. 20, 1961." should read as, --Stock et al., "Rates, Relative Rates and Product Distributions for the Non-catalytic Chlorination of Benzene, Toluene and t-Butylbenzene in Certain Non-aqueous Non-hydroxylic Solvents. The Influence of Solvent on the Reaction and the Baker-Nathan Effect," Journal of the American Chemical Society 83 (22): 4605-4609, Nov. 20, 1961.--

Signed and Sealed this
Eighth Day of March, 2011

David J. Kappos
*Director of the United States Patent and Trademark Office*